(12) United States Patent
Omura et al.

(10) Patent No.: US 8,596,276 B2
(45) Date of Patent: Dec. 3, 2013

(54) NASAL RESPIRATORY MASK SYSTEM

(75) Inventors: Keiko Omura, Tokyo (JP); Masahide Takishita, Tokyo (JP); Tongoh Chin, Tokyo (JP); Hideharu Shimura, Osaka (JP); Shinya Fujimoto, Osaka (JP); Naoki Kurai, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 1071 days.

(21) Appl. No.: 12/309,322

(22) PCT Filed: Jul. 17, 2007

(86) PCT No.: PCT/JP2007/064078
§ 371 (c)(1),
(2), (4) Date: Oct. 23, 2009

(87) PCT Pub. No.: WO2008/010484
PCT Pub. Date: Jan. 24, 2008

(65) Prior Publication Data
US 2010/0043800 A1    Feb. 25, 2010

(30) Foreign Application Priority Data

Jul. 18, 2006   (JP) ................................. 2006-195543

(51) Int. Cl.
*A61M 16/06* (2006.01)
*A62B 18/02* (2006.01)

(52) U.S. Cl.
USPC ............. 128/207.13; 128/206.21; 128/206.24

(58) Field of Classification Search
USPC ............. 128/200.24, 204.18, 205.25, 206.16, 128/206.21, 206.24, 206.26, 206.28
See application file for complete search history.

(56) References Cited

U.S. PATENT DOCUMENTS 2,011,733 A * 8/1935 Shindel .................... 128/206.24
2,444,417 A * 7/1948 Bierman .................. 128/201.19
(Continued)

FOREIGN PATENT DOCUMENTS

CN       1681553 A       10/2005
CN       1735439 A       2/2006
(Continued)

OTHER PUBLICATIONS

Office Action from Japan Patent Office for application serial No. 2008-525859 dated May 24, 2011.

(Continued)

*Primary Examiner* — Justine Yu
*Assistant Examiner* — Valerie L Skorupa
(74) *Attorney, Agent, or Firm* — Rader, Fishman & Grauer PLLC

(57) ABSTRACT

A light weight nasal respiratory mask system securing airtightness of a mounting section between a nasal mask and a frame is provided.

A nasal respiratory mask system contacting the face of a user to supply respiratory gas under positive pressure to the nose of a use and comprising at least a nasal mask, a frame and a retention wire, in which the nasal mask is a tubular member composed of a face contacting section constructed from an elastic body at one end of an opening and a frame mounting section constructed from an elastic body at the other end of the opening, the frame is a molded part with an internal space capable of communicating between a hose to supply positive pressure gas and the nasal mask and has a mechanism connectable with the hose to supply positive pressure gas and a nasal mask mounting section allowing the nasal mask to mount on periphery thereof, the frame mounting section of the nasal mask is mounted to cover from the outside the nasal mask mounting section of the frame, and at least part of the retention wire has a structure to tighten the frame mounting section of the nasal mask to the side of nasal mask mounting section of the frame.

13 Claims, 3 Drawing Sheets

(56) References Cited

U.S. PATENT DOCUMENTS

| | | | |
|---|---|---|---|
| 5,243,971 A | 9/1993 | Sullivan et al. | |
| 5,349,949 A * | 9/1994 | Schegerin | 128/206.24 |
| 5,918,598 A * | 7/1999 | Belfer et al. | 128/206.25 |
| 6,491,034 B1 * | 12/2002 | Gunaratnam et al. | 128/204.18 |
| 6,615,834 B2 * | 9/2003 | Gradon et al. | 128/207.11 |
| 6,789,543 B2 * | 9/2004 | Cannon | 128/207.18 |
| 6,823,869 B2 | 11/2004 | Raje et al. | |
| 7,523,754 B2 | 4/2009 | Lithgow et al. | |
| 2004/0025882 A1 * | 2/2004 | Madaus et al. | 128/206.27 |
| 2004/0065328 A1 * | 4/2004 | Amarasinghe et al. | 128/206.27 |
| 2004/0118406 A1 | 6/2004 | Lithgow et al. | |
| 2004/0134497 A1 | 7/2004 | Gunaratnam et al. | |
| 2004/0182398 A1 | 9/2004 | Sprinkle et al. | |
| 2006/0076019 A1 * | 4/2006 | Ho | 128/206.24 |
| 2006/0118117 A1 * | 6/2006 | Berthon-Jones et al. | 128/206.21 |
| 2006/0260614 A1 * | 11/2006 | Biener et al. | 128/206.21 |
| 2009/0178679 A1 | 7/2009 | Lithgow et al. | |

FOREIGN PATENT DOCUMENTS

| | | | |
|---|---|---|---|
| EP | 1027905 | A2 | 8/2000 |
| EP | 1099452 | A2 | 5/2001 |
| JP | 11-000397 | A | 1/1999 |
| JP | 2000-279520 | A | 10/2000 |
| JP | 2003-502118 | A | 1/2003 |
| JP | 2004-522481 | A | 7/2004 |
| JP | 2005-111287 | A | 4/2005 |
| TW | 462893 | B | 11/2001 |
| WO | WO-00/78383 | A1 | 12/2000 |
| WO | WO 02/45784 | A1 | 6/2002 |
| WO | WO 03/035156 | A2 | 5/2003 |
| WO | WO 03/059427 | A1 | 7/2003 |
| WO | WO-2004/041342 | A1 | 5/2004 |
| WO | WO 2004/096332 | A1 | 11/2004 |
| WO | WO-2005/063327 | A1 | 7/2005 |

OTHER PUBLICATIONS

International Search Report mailed on Oct. 16, 2007.
Office Action for Chinese Patent Application No. 2011010800038740, dated Jan. 12, 2011.
Extended European Search Report issued in EP Application No. 07790840.8, dated Dec. 6, 2012.
Taiwan Office Action issued on Feb. 1, 2013 in corresponding Application No. 96126001.

* cited by examiner

NASAL RESPIRATORY MASK SYSTEM

TECHNICAL FIELD

The present invention relates to a nasal respiratory mask system used for continuous positive airway pressure (CPAP) therapy suitable for the treatment of sleep apnea syndrome, nasal intermittent positive pressure ventilation (NIPPV) therapy suitable for ventilatory insufficiency, and the like.

BACKGROUND ART

One of the most effective therapeutic methods for sleep apnea syndrome is a nasal continuous positive airway pressure (CPAP) method, in which a respiratory assist device is adopted to supply positive pressure gas at about 400 to 2000 Pa to the nasal cavity of a user during sleep. In recent years, devices with a function to control a pressure automatically responding to an occurrence state of apnea during therapy have also been used. One of the most effective therapeutic methods for ventilatory insufficiency is a nasal intermittent positive pressure ventilation (NIPPV) method, in which a respiratory assist device is adopted to supply intermittent positive pressure gas at about 400 to 2400 Pa to the nasal cavity of a user.

When these types of equipments are used for treatments, a nasal respiratory mask system composed of a nasal mask (also called "nasal mask cushion" or "cushion") tightly sealing the face of a user and having a hollow shape and of a frame retaining the nasal mask at a predetermined position and having a mechanism to connect with a hose that leads a positive pressure gas is generally used to continuously maintain positive pressure to the nasal cavity of a user. Such a nasal mask system then tightly seals the face of a user by the tension of a strap (including a headgear) (see, for example, Patent Document 1).

Patent Document 2 discloses mounting a brace composed of a wire engageable with a frame section in a nasal respiratory mask system. Such a brace may serve as a mounting site for a strap (including a headgear), but has no function to reinforce the fixing a nasal mask to the frame.

Patent Documents 3 and 4 disclose a forehead support supporting a nasal mask system, in which a forehead pad is attached to such a forehead support. However, such a forehead support is attached to a connection section of a hose for respiratory gas.

Patent Document 5 describes a member called a circular "frame" mounted on a surrounding of "shell/cushion". However, such a "frame" can be engaged only with a channel provided in "shell/cushion", but has no function to fix a cushion to a shell. Even in preferred embodiments, both shell and cushion are primarily integrated in one piece.

Patent Documents 6 also describes a member called circular "frame" mounted on a surrounding of a "curved body", but lacks a function to fix a nasal mask to the "curved body".

Patent Document 1: Japanese Patent Laid-Open Publication No. H11-397.
Patent Document 2: WO 02/045784
Patent Document 3: WO 03/035156
Patent Document 4: WO 03/059427
Patent Document 5: WO 04/096332
Patent Document 6: WO 03/035156

DISCLOSURE OF INVENTION

Problems to be Solved by Invention

An object of the present invention is to solve at least one of problems by providing as a whole a light weight nasal respiratory mask system while practically minimizing leakage of gas from an interface section between a frame and a nasal mask, providing a nasal respiratory mask system for a user to easily deform to closely conform to a facial shape of a user, providing a nasal respiratory mask system with a structure high in shape-recovery restoring force and easily absorbing body movements and providing a nasal respiratory mask system enabling a strap to be attached easily.

Means to Solve the Problems

The present invention is a nasal respiratory mask system contacting with the face of a user to supply respiratory gas under positive pressure to the nose of the user, comprising at least a nasal mask, a frame and a retention wire; in which the nasal mask is a tubular member composed of a face contacting section with one opening end constructed from an elastic body and a frame mounting section with the other opening end constructed from an elastic body, the frame is a molded part with an internal space capable of communicating between a hose to supply positive pressure gas and the nasal mask and has a mechanism connectable with the hose to supply positive pressure gas and a nasal mask mounting section enabling to mount the nasal mask on periphery thereof, a frame mounting section of the nasal mask is mounted to cover the nasal mounting section of the frame from the outside, and at least part of the retention wire has a structure to tighten the frame mounting section of the nasal mask to the side of the nasal mask mounting section of the frame.

Effect of Invention

The nasal respiratory mask system of the present invention can effectively prevent gas leak from an interface section between a frame and a nasal mask, because at least part of a retention wire has a structure to tighten a frame mounting section of the nasal mask to the side of the nasal mask mounting section of the frame. Accordingly, gas leakage from an interface coupling section of the frame and the nasal mask can be controlled to a minimum level even if their wall thickness is reduced, so that as a whole a lightweight nasal mask can be attained.

The nasal respiratory mask system can be obtained depending on a shape or material of a retention wire, which is easily deformed by a user her/himself to conform to a facial shape of the user. This allows the user, for example, to adjust unevenness of mask contact force to the face.

A retention wire can give the nasal respiratory mask system with a structure easily absorbing body movement because it has high restoring force from deformation.

Furthermore, an appropriate attaching position for a strap can be provided depending on a shape of the retention wire, leading to provide the nasal respiratory mask system with an easy-to-use strap attaching structure.

Washing insides of the nasal mask and the frame can be also easier as compared to an integrated unit of the nasal mask and the frame, because of having a structure to detach the nasal mask and the frame.

Furthermore, by manufacturing the nasal mask and the frame separately, the production is easier as compared to an integrated unit of the nasal mask and the frame and leads to reducing the manufacturing cost.

DESCRIPTION OF SYMBOLS

Figure 1:
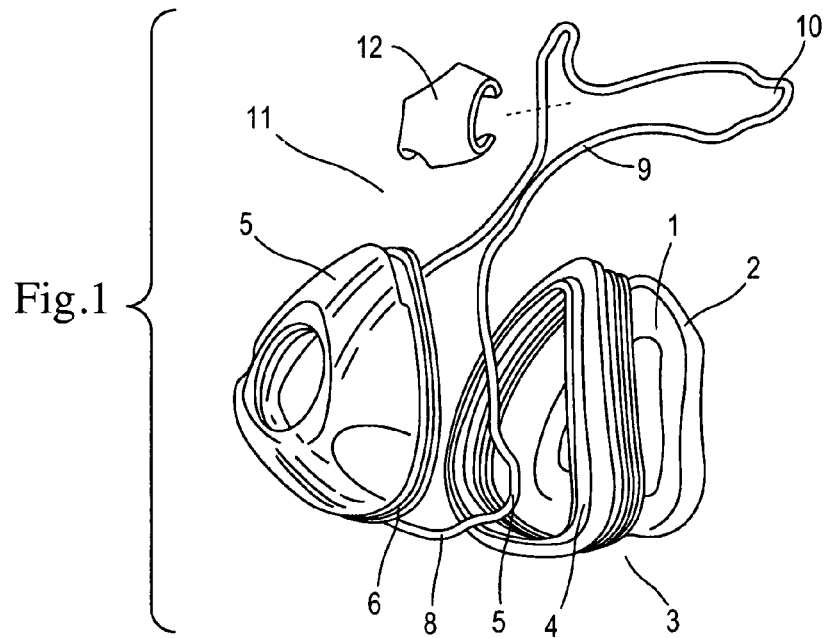
FIG. 1 is a drawing to illustrate the constitution of the nasal respiratory mask system of the present invention.

1. Nasal mask body
2. Face contacting section of nasal mask
3. Nasal mask
4. Frame mounting section
5. Frame
6. Nasal mask mounting section
7. Hose attaching section to supply respiratory gas under positive pressure
8. Retention wire
9. Protrusion of retention wire (clip attaching section)
10. Protrusion of retention wire (strap attaching section)
11. Nasal respiratory mask system
12. Clip
13. Hose to supply respiratory gas under positive pressure
14. Member to treat strap end
15. Strap
16. Pad

BEST MODE TO CARRY OUT THE INVENTION

The present invention is a nasal respiratory mask system contacting with the face of a user to supply respiratory gas under positive pressure to the nose of a user and comprising at least a nasal mask, a frame and a retention wire, in which said nasal mask is a tubular member composed of a face contacting section with one opening end constructed from an elastic body and a frame mounting section with the other opening end constructed from an elastic body, said frame is a molded part with an internal space capable of communicating between a hose to supply positive pressure gas and the nasal mask and has a mechanism to connect with the hose to supply positive pressure gas and a nasal mask mounting section to mount the nasal mask on periphery thereof, a frame mounting section of the nasal mask is mounted to cover the nasal mask mounting section of the frame from the outside and at least part of a retention wire has a structure to tighten the frame mounting section of the nasal mask to the side of the nasal mask mounting section of the frame. Such a nasal respiratory mask system is worn on the head of the user with a strap or headgear and connected with a supply hose of respiratory gas under positive pressure.

Both ends of such a nasal mask are made from an elastic body and hollow, that is, tubular, through which respiratory gas under positive pressure passes, and are required to have a structure, of which an end of the opening can tightly seal around the nose of a user and the other end of the opening is suitable to attach to the frame. Such a structure suitable to attach to the frame refers to a shape covering from the outside a nasal mask mounting section in periphery of the frame opening. Rubbery products are preferred, particularly silicone rubbers are preferred as such an elastic material.

Periphery of the opening end at the side of a user is often substantially molded in an isosceles triangular shape to reflect a nasal shape, since the nasal mask secures airtightness of respiratory gas under positive pressure by pressing around the nose of a user (see WO 98/04310 and Japanese Patent Laid-Open Publication No. H10-337327). A shape of the nasal mask as a whole is preferably a substantially hollow triangular prismatic form to reflect the shape of the opening end at the side of a user, but may have other shapes as long as the airtightness is secured.

On the other hand, a middle section between both ends of the nasal mask is not necessarily constructed from an elastic body. Such a middle section may involve a mechanism to absorb misalignment of the nasal respiratory mask system caused by body movement, for example, a bellows structure (see Japanese Patent Laid-Open Publication No. H11-397).

The nasal mask may be molded in a single piece, but a combination of a plurality of members may be used as long as the respiratory gas under positive pressure does not leak.

The frame in the present invention has at least a structure to connect with a hose to supply respiratory gas under positive pressure and an opening to supply the respiratory gas under positive pressure to the nasal mask, of which the nasal mask mounting section is provided around periphery of the opening. That is, such nasal mask mounting section has a short tubular structure, in which the nasal mask is mounted on periphery of the tubular section.

As a mechanism to connect with the hose to supply respiratory gas under positive pressure, a mechanism known by those skilled in the art may be used as long as the mechanism does not practically leak the respiratory gas under positive pressure. For example, such mechanism is disclosed in WO 04/022147.

The above-mentioned frame mounting section of the nasal mask covers the nasal mask mounting section of the frame from the outside. The whole of peripheral edge of the nasal mask mounting section of the frame is required to be covered to secure the airtightness of respiratory gas under positive pressure, but both sections may be only partly overlapped each other in a mounting direction as long as they have airtightness. As a shape for the nasal mask mounting section of the frame and the frame mounting section of the nasal mask, which are required to be conformed each other in order to keep the airtightness, but the shape is no object as long as the airtightness is secured, for example, a short cylindrical shape or a hollow triangular prismatic shape may be accepted.

Furthermore, a channel to receive the frame mounting section of the nasal mask may be provided around the nasal mask mounting section of the frame as well as a part of the frame mounting section of the nasal mask may have an insert shape into the channel. This makes the nasal mask difficult to come off the frame, coupled with tightening force by the retention wire.

Any frame shape in the present invention may be used as long as it is suitable to fix the nasal mask. It is generally a bowl or dome shape, but may be planar. A triangular dome shape may be appropriate as a shape of the frame corresponding to a typical shape of the nasal mask with a hollow triangular prismatic shape as described above, but such shape needs not be essential as long as it has a function as the nasal respiratory mask system.

As described above, such frame serves to fix the nasal mask and the hose to supply respiratory gas under positive pressure so that it has to be made from hard materials within the required limit. It is generally constructed with plastics, for example, polycarbonate.

The retention wire in the present invention is to tighten from the outside at least part of periphery of an overlapped section between the nasal mask mounting section of the frame above and the frame mounting section of the nasal mask above. Shape restoring force provided in the retention wire itself is used for such tightening.

The retention wire may have an open or closed structure as long as tightening force is fully exerted, but a closed loop structure is generally used. In case of an open structure, processing such as fixing both ends has to be carried out in order to exert tightening force. The retention wire may be a single loop or multiple-layered loops, but a single loop is preferably used. When multiple-layered loops are used, the retention wire(s) may be bundled with other wires, yarns and the like. The retention wire may be also covered with plastics, for example, polyvinyl chloride or with cloths, or its surface may be coated with plating, paint or the like.

A material used for the retention wire is not particularly limited as long as the tightening force described above is exerted by the restoring force from deformation, but preferably include metals, particularly titanium, stainless steel, aluminum, duralumin, magnesium, GUM METAL, NT alloy, brass, shape memory alloys and resins. Its size varies depending on the material, and when the material is titanium, the diameter is around in the range of 0.5 to 2 mm.

A part of the retention wire in the present invention may have a protrusion away from the nasal mask. Such a protrusion of the retention wire may have a mechanism to intensify tightening force of the nasal mask to the frame by the retention wire.

Such a mechanism to intensify tightening force includes as an example a mechanism positioning the part of the protrusion of the retention wire by a member having at least two hooks engageable with the retention wire, that is, intensifying the tightening force by providing a clip on the protrusion of the retention wire. Materials used for the clip include hard plastics such as polyacetal, soft rubbers such as silicone rubber and metals such as stainless steel, but are not particularly limited as long as they have a function for positioning. Further, tightening force in the nasal mask can be adjusted, when the mechanism has at least two hooks engageable with the retention wire and adjustable with a distance between the two hooks by a screw mechanism.

In addition, a protrusion of the retention wire may also be provided for other purpose, that is, the protrusion may be positioned in front of the forehead of a user of the nasal respiratory mask system to have a role on serving a room for controlling the pressure of the nasal respiratory mask system to the face. In such a case, a pad may be further provided on the side of forehead of the protrusion of the retention wire. This eases pain caused by directly pressing the retention wire to the forehead of a user. The pad may have a structure to be fixed by tightening with the protrusion of the retention wire, leading to an advantage, in which a complex attaching mechanism is not required. However, other structure may be used as long as the pad can be attached to the protrusion of the retention wire.

Such a protrusion of the retention wire located in front of the forehead of a user may be deformable. When the protrusion is deformable, a user her/himself can adjust the wear feeling by deforming its shape to conform to her/his face to change a sealing level. For example, depending on a facial shape of a user, it is possible to reduce disproportionate distribution of sealing force between a forehead side and a mouth side of the face where the nasal mask contacts.

The protrusion of the retention wire may also be used for other purpose. The nasal respiratory mask system in the present invention is worn on the head of a user by a strap including a headgear. Therefore, a strap attaching site for this purpose has to be provided. Such a strap attaching site has been conventionally provided on a frame, but may be on the frame or the protrusion of the retention wire, or on both of them in the nasal respiratory mask system in the present invention. When the strap attaching site is particularly provided on the protrusion of the retention wire, the protrusion of the retention wire is suitable to place in front of the forehead or the side of the nose of a user of the nasal respiratory mask system, but its location is no object as long as it has a function to wear on the head of a user. A method to attach the strap to the protrusion of the retention wire may include direct attachment of the strap to the protrusion of the retention wire or attachment of a simple member engageable with the protrusion of the retention wire to the strap, leading to an advantage, in which a complex attaching mechanism is not required.

When a plurality of the protrusions of the retention wire are used, each of them can be used for different purposes, but one of the protrusions of the retention wire may be simultaneously used for several purposes described above. For example, a mechanism to intensify tightening force is provided on a part of the protrusion of the retention wire and the strap attaching site is provided on other site of the same protrusion.

EXAMPLE

A specific example of the present invention is further detailed with reference to drawings below.

FIG. 1 demonstrates an example of nasal respiratory mask system 11 of the present invention. Nasal mask 3 (illustrated as transparent, hereinafter the same.) constituted from nasal mask body 1 composed of a tubular elastic body, to which similarly elastic face contacting section 2 of the nasal mask attaches. Periphery of an opening end placed opposite to such a face contacting section 2 of nasal mask 3 serves as frame mounting site 4.

Frame 5 is provided with nasal mask mounting section 6. Frame mounting section 4 of the nasal mask is positioned at periphery of nasal mask mounting section 6 of the frame to be tightened by retention wire 8 from the outside. Positional relation of them is demonstrated in a cross-sectional view in FIG. 4. Hose attaching section 7 is also attached to frame 5 to supply respiratory gas under positive pressure and hose 13 to supply respiratory gas under positive pressure (not shown) is connected with hose attaching section 7 to supply respiratory gas under positive pressure.

In nasal respiratory mask system 11 in FIG. 1, protrusion 9 (clip attaching section) and protrusion 10 (strap attaching section) are provided on retention wire 8, while the former has a strap attaching section on other site in the same protrusion.

Clip 12 made of a hard member with three hooks engageable with the retention wire is inserted into a protrusion of the retention wire 9 (clip attaching section) to position a part of the protrusion of the retention wire, intensifying tightening force of frame mounting section 4 of the nasal mask towards nasal mask mounting section 6 of the frame by the retention wire. Furthermore, tightening force towards pad 16 attached to the protrusion of retention wire 9 (clip attaching section) is intensified.

Figure 2:
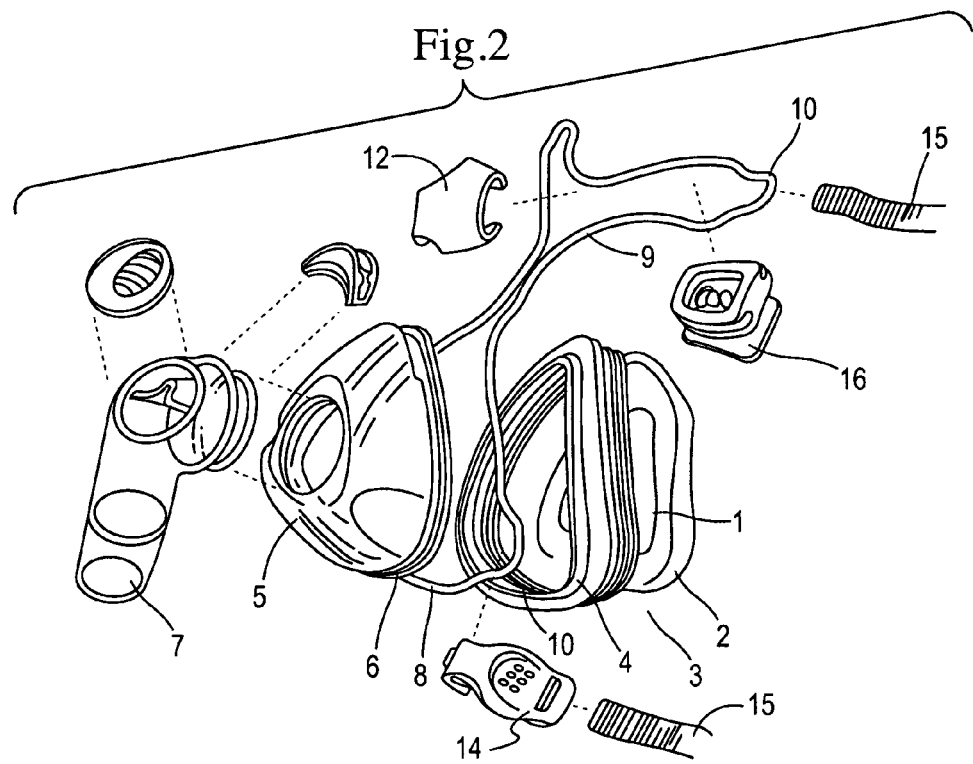
FIG. 2 is a drawing to illustrate the nasal respiratory mask system of the present invention and a member connected thereto.
Figure 3:
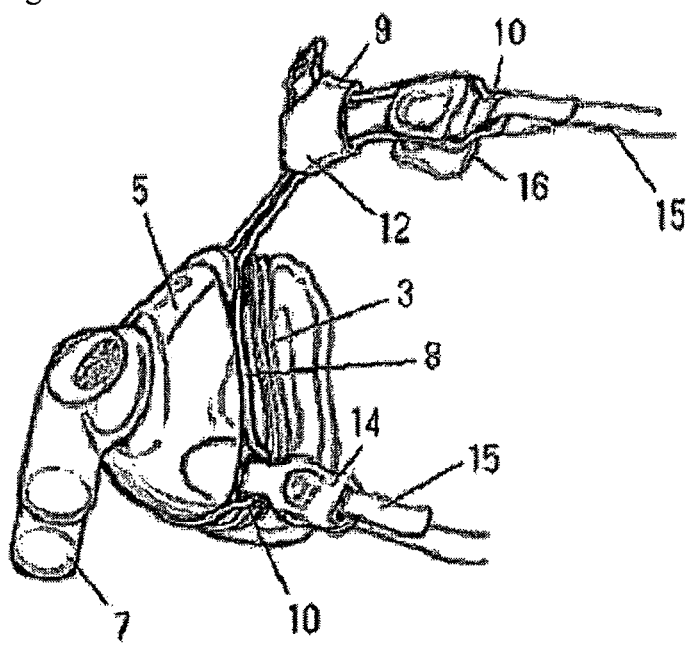
FIG. 3 is a drawing to show the nasal respiratory mask system of the present invention and the member connected thereto assembled together.
Figure 4:
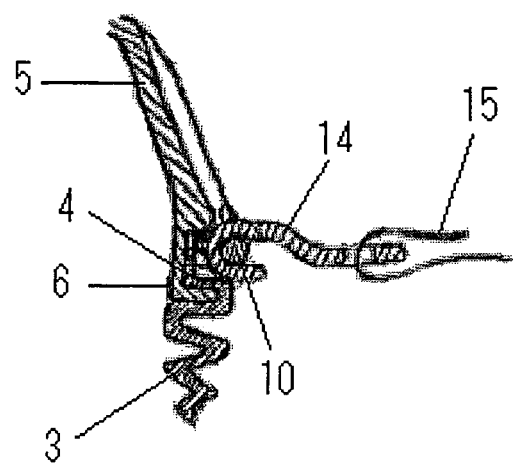
FIG. 4 is a cross-sectional diagram to illustrate an example of relative position between the nasal mask mounting section of a frame, a frame mounting section of the nasal mask and a retention wire in the present invention.
Figure 5:
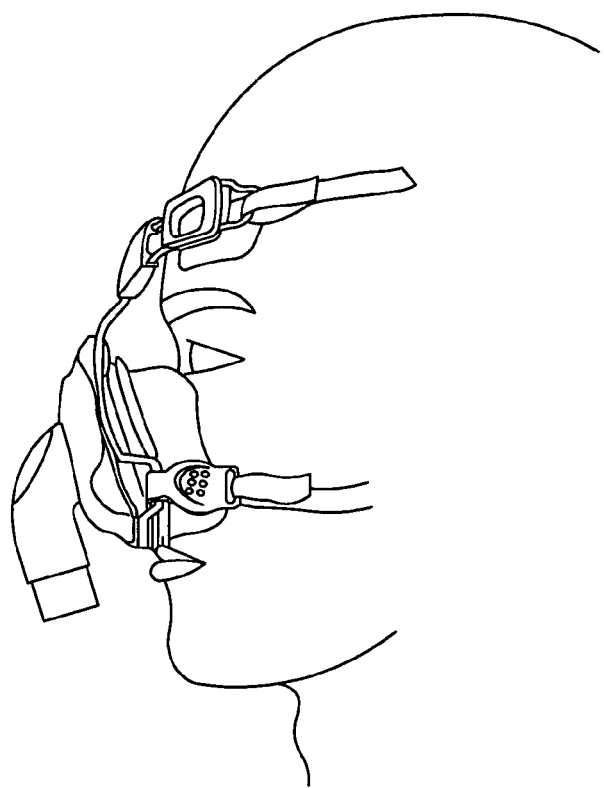
FIG. 5 is a drawing to show the nasal respiratory mask system of the present invention fitted to a user.

On the other hand, strap 15, to which member to treat a strap end 14 is attached at the end is engaged with the protrusion of retention wire 10 (strap attaching section) (see FIGS. 2 and 4).

Figure 6:
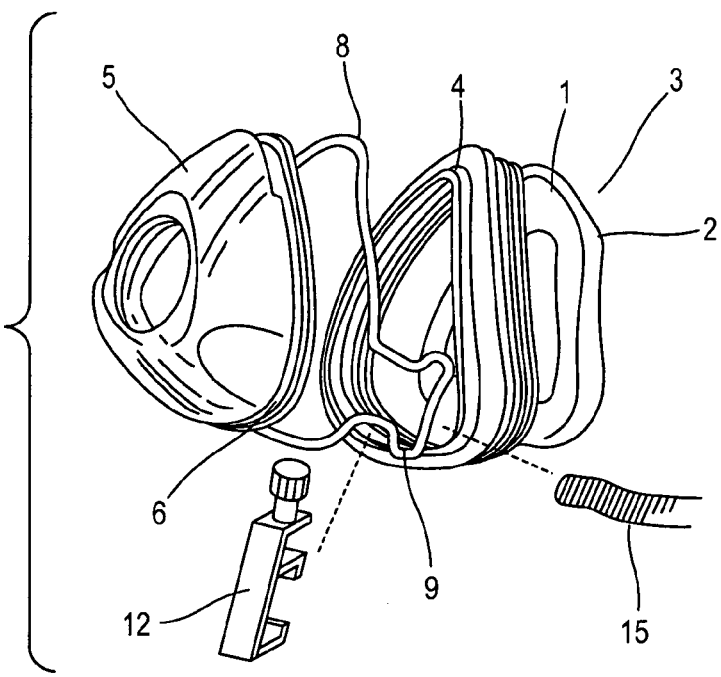
FIG. 6 is a drawing to illustrate the other constitution of the nasal respiratory mask system of the present invention.

FIG. 6 demonstrates one example of other embodiments of the nasal respiratory mask system 11 of the present invention. It is similarly composed as example shown in FIG. 1 of nasal mask 3, frame 5, hose attaching section to supply respiratory gas under positive pressure 7 (not shown) and hose to supply respiratory gas under positive pressure gas 13 (not shown). In nasal respiratory mask system 11 in FIG. 6, retention wire 8 is provided with protrusion 9 (clip attaching section) and a strap attaching section in other site of the same protrusion. A protrusion of retention wire 9 (clip attaching section) is provided at two sites in front of the sides of the nose of a user when wearing nasal respiratory mask 11 (only one site is shown). Clip 12 has two hooks engageable with the protrusion of retention wire 9 (clip attaching section) and a screw structure that adjusts a distance between two hooks.

Clips 12 are each inserted into the protrusion of retention wire 9 (clip attaching section) at two sites to position a part of the retention wire, intensifying the tightening force of frame mounting section 4 of the nasal mask towards nasal mask mounting section 6 of the frame. Further, by adjusting a screw of clip 12, the tightening force above is adjusted.

The protrusion of retention wire 9 (clip attaching section) in FIG. 6 is directly engaged with strap 15.

Industrial Applicability

The present invention provides a nasal respiratory mask system used in CPAP therapy, NIPPV therapy and the like.

The invention claimed is:

1. A nasal respiratory mask system adapted to contact with the face of a user with a face-applying force to supply respiratory gas under positive pressure to the nose of the user, comprising at least a nasal mask, a frame, a clip device and a retention wire in a form of a loop, said nasal mask being a tubular member composed of a face contacting section constructed from an elastic body at one end of an opening and a frame mounting section constructed from an elastic body at the other end of the opening, said frame being a molded part with an internal space capable of communicating between a hose to supply respiratory gas under positive pressure and the nasal mask, having a mechanism to connect with the hose to supply positive pressure gas and a nasal mask mounting section allowing the nasal mask to mount on a periphery thereof, wherein the retention wire has a frame-retaining section and a protrusion section integrally connected to the frame-retaining section, wherein the frame receives the nasal mask in a manner that the nasal mask mounting section contacts and surrounds the frame mounting section with the frame-retaining section of the retention wire in contact with and squeezing the nasal mask mounting section onto the frame mounting section with a tightening force, and wherein the clip device is operative with the protrusion section of the retention wore such that the clip device captures and contacts adjacent pieces of the protrusion section and urges the adjacent pieces of the protrusion section together thereby increasing the tightening force of the mask mounting section onto the frame mounting section.

2. The nasal respiratory mask system according to claim 1, wherein the clip device to intensify the tightening force of the nasal mask to the frame by the retention wire is to position part of the protrusion of the retention wire by a clip device structure with at least two hooks engageable with the adjacent pieces of the protrusion section of the retention wire.

3. The nasal respiratory mask system according to claim 1, wherein the clip device to intensify tightening force of the nasal mask to the frame by the retention wire has at least two hooks engageable with the adjacent pieces of the protrusion section of the retention wire and a distance between the two hooks is adjustable by a screw mechanism.

4. The nasal respiratory mask system according to any one of claims 1 to 3, wherein the protrusion of the retention wire is positioned in front of the forehead of a user when wearing the nasal respiratory mask system.

5. The nasal respiratory mask system according to claim 4, wherein a pad is provided on the forehead side of the protrusion of the retention wire.

6. The nasal respiratory mask system according to claim 4, wherein the protrusion of the retention wire positioned in front of the forehead can be deformed to suitably conform to the facial shape of a user.

7. The nasal respiratory mask system according to any one of claims 1 to 3, wherein the protrusion of the retention wire is positioned in front of a side of the nose of a user when wearing the nasal respiratory system.

8. The nasal respiratory mask system according to any one of claims 1 to 3, wherein the retention wire is a single closed loop.

9. The nasal respiratory mask system according to any one of claims 1 to 3, wherein the frame and/or the protrusion of the retention wire is provided with a strap attaching section.

10. The nasal respiratory mask system according to any one of claims 1 to 3, wherein the frame is a dome shape.

11. The nasal respiratory mask system according to claim 1, wherein the tightening force and the face-applying force are completely independent of one another.

12. The nasal respiratory mask system according to claim 11, wherein increasing the tightening force of the nasal mask mounting section onto the frame mounting section has no impact on the face applying force.

13. The nasal respiratory mask system according to claim 1, wherein the clip device captures and contacts at least two adjacent pieces of the protrusion section and urges the at least two adjacent pieces of the protrusion section together.

* * * * *